United States Patent [19]

Graupe

[11] 4,209,860
[45] Jul. 1, 1980

[54] SYSTEM AND METHOD FOR MULTIFUNCTIONAL CONTROL OF UPPER LIMB PROSTHESIS VIA EMG SIGNAL IDENTIFICATION

[75] Inventor: Daniel Graupe, Fort Collins, Colo.

[73] Assignee: The United States of America as represented by the Administrator of Veterans' Affairs, Washington, D.C.

[21] Appl. No.: 877,379

[22] Filed: Feb. 13, 1978

[51] Int. Cl.² ........................... A61F 1/00; A61F 1/06
[52] U.S. Cl. ......................................................... 3/1.1
[58] Field of Search ............................. 3/1.1, 12–12.7

[56] References Cited

U.S. PATENT DOCUMENTS

4,030,141 6/1977 Graupe ...................................... 3/1.1

Primary Examiner—Ronald L. Frinks
Attorney, Agent, or Firm—Browdy and Neimark

[57] ABSTRACT

A system for controlling the operation of an electrically powered prosthetic appliance which replaces an amputee's missing limb. The method employed consists of conducting electromyographic (EMG) signals from the stump of the missing limb and processing the signals so as to reduce them to a near minimum number of linear time series model parameters effective to differentiate between each of the several functions performed by the missing limb from each other function thereof. A filter array carried by the amputee subsequently employs the identified parameters such that each individual filter of the array is tuned according to a set of parameters related to one of the limb functions considered. The myoelectric (EMG or ME) signal as obtained at a surface electrode worn by the amputee is fed to each filter of the above array of filters, and the outputs of these various filters are used for a decision by the system as to which limb function should be actuated. In another realization, identification of partial correlation coefficients of the ME signal is performed. These coefficients are stored in memory per each limb function, and during normal operation the partial correlation parameters for the current ME signal are compared with those in memory to determine which limb function is to be actuated.

13 Claims, 3 Drawing Figures

SYSTEM AND METHOD FOR MULTIFUNCTIONAL CONTROL OF UPPER LIMB PROSTHESIS VIA EMG SIGNAL IDENTIFICATION

FIELD OF THE INVENTION

This invention relates to EMG-based methods and apparatus for actuating a prosthetic appliance, and more particularly to EMG-based systems utilizing time series functions of the EMG signal to differentiate between specific intended limb functions of the appliance.

BACKGROUND OF THE INVENTION

The present invention is concerned with the problem of controlling artificial limbs in cases where several limb functions require control. These situations are of importance especially to above-elbow upper extremity amputees. Here, classical EMG (myoelectric) controllers have failed in the past, since they were based only on determining the existence or non-existence of an EMG signal. Recent work performed by others has approached the multifunctional control problem by using a large number of electrodes, though still considering only a limited part of the EMG spectrum. The approach employed in the present invention is based on that described in U.S. Pat. No. 4,030,141 to Daniel Graupe, employing consideration of the whole spectrum of the EMG signal via identifying its time series model. However, the present invention subsequently employs parallel filtering to discriminate between the various limb functions of interest to achieve fast discrimination and control, as required for practical applications, since this allows the basic identification procedure itself to be performed off line.

Multifunctional control of artificial upper extremities via using myoelectric (EMG) signals is of major importance in the above-mentioned cases of above-elbow amputees. For solving this problem it is essential to distinguish between the different limb functions to be controlled from the pattern of the myoelectric signal at some or several stump locations. Hence, differences in pattern of myoelectric signals related to various limb functions (i.e., elbow bending, elbow extension, wrist pronation, wrist supination, grasp, etc.), as taken at one or several stump muscles, must be detected. Although such differences do exist, they are hardly obvious to the naked eye of even an expert. Two major approaches to solve this problem have been suggested. One, based on the works of Lawrence (1) and of Lyman et al (2), requires mapping of many (ten or more) electrode locations at each of which the EMG function is strongly correlated with a single limb function. It thus employs the low frequency characteristics of the EMG signals and of their mapping or distribution over the various electrode locations. Furthermore, due to the number of electrode sites required, this method is limited to amputees with little nerve and muscle damage to their stumps and with relatively long stumps. The other approach, based on the work of Graupe et al (3), (4), requires a far smaller number of electrode locations (one to three) since it aims at recognition at locations where even very weak correlations between the measured signal and (more than one) limb functions may exist. This method takes advantage of cross-talk between signals relating to different limb functions, in contrast to other methods where this cross-talk is gotten rid of and is disturbing. This method is thus suitable for amputees with severe nerve and muscle damage in their stumps. Moreover, this method is concerned with the complete spectrum since it implies that the complete linear information content of the EMG signal is considered (i.e., at all frequencies. It is thus more efficient in terms of utilizing the information of the EMG signal, such that less electrode locations need be considered, though at the price of requiring finer detection. It is to be noted that the above correlation with more than one limb function is due to the spatial integration effect of muscle fiber and skin tissue that affects the signal as measured by surface electrodes (5).

The following publications, to which reference by number is made herein, appear to show the present state of the art:

1. Lawrence, P. "Computer Design and Simulation of a Myoelectric System for Controlling a Multifunctional Prosthetic Hand". Proc. Symp. on Pattern Recognition and Mathematical Image Processing. Chalmers University, Goeteborg, Sweden, August, 1972.
2. Lyman, T., Freedy, A., and Solomonow, M., "Studies Toward a Practical Computer-Aided Arm Prosthesis System". Bull. Prosth. Res. pp 213-225, Fall Issue, 1974.
3. Graupe, D. and Cline, W. K., "Functional Separation of EMG Signals via ARMA Identification Methods for Prosthetic Control Purposes". IEEE Trans. on Systems, Man and Cybernetics. Vol. SMC-5, pp. 252-259, March 1975.
4. Graupe, D., "Control of Upper Limb Prosthesis in Several Degrees of Freedom". Bull. Prosth. Res. pp 226-236, Fall Issue, 1974.
5. Brody, G., Balasubramanian, R., and Scott, R. N., "A Model for Myoelectric Signal Generator", Med. & Bio. Eng. pp 29-41, Jan. 1974.
6. Graupe, D., "Identification of Systems", 2nd Edition, R. E. Krieger Publishing Co., New York, N.Y., 1976.
7. Rasch and Burke, "Kinesiology and Applied Anatomy", 5th Edition, H. Kimpton Publishers, London, (p.55)
8. Papoulis, A., "Probability, Random Variables, and Stochastic Processes", McGraw Hill, New York, N.Y., 1965, (Chapter 16).
9. Graupe, D., Krause, D. J., and Moore, J. B., "Identification of Auto-regressive Moving-Average Parameters of Time Series", IEEE Trans. on Aut. Cont., Vol. AC-20, pp 104-107, Feb. 1975.
10. Saradis, G. N., "Comparison of Five Popular Identification Algorithms—A Survey", Proc. Decision and Control Conf., New Orleans, 1972.
11. Luenberger, D. G., "Optimization by Vector Space Methods", John Wiley and Sons, New York, N.Y., 1969.
12. Datel Systems, Inc. "Engineering Product Handbook", No. AT 75408.
13. Intel Corp., "Intel 8080 Microcomputer Systems Manual", 1975.
14. Graupe, D., U.S. Pat. No. 4,030,141.

SUMMARY OF THE INVENTION

The present invention is based on the general approach set forth in the U.S. Pat. No. 4,030,141 to D. Graupe, but with the objects of providing more rapid function separation and recognition, with the utilization of fast function separation and recognition algorithms and microcomputer hardware, with speed providing recognition within about 0.2 second, and with reduced weight, volume and cost.

Accordingly, a main object of the present invention is to provide an improved method and apparatus for controlling artificial limbs which overcomes the deficiencies of the prior art systems.

A further object of the invention is to provide an improved method and apparatus for controlling artificial limbs in several degrees of freedom via identification and discrimination of EMG signals, employing a function separation algorithm based on time series model identification as in U.S. Pat. No. 4,030,141, but with an improved discrimination approach and with an improved and more efficient identification subroutine, yielding substantially reduced recognition time.

The present invention differs from the system forming the subject matter of U.S. Pat. No. 4,030,141 by reason of the fact that it confines to the calibration phase of the method used all the necessary identification of limb functions as well as the definition of those conditions which must be met before the corresponding function in the prosthesis is initiated, thereby simplifying as well as speeding up the control mode due to the elimination of the relatively slow identification procedure therefrom.

U.S. Pat. No. 4,030,141 discloses an EMG-actuated system for controlling artificial limbs which is characterized by the analysis of the EMG signals from the patient and the comparison thereof with stored historical data by means of a patient-borne microprocessor. This system functions quite well and its major shortcoming lies in the fact that the computation time necessary to identify and initiate a function is somewhat longer than it should be. This is because the limb function identification phase of the method is carried out both in the control mode and during the calibration mode, rather than only during the calibration mode, and since this phase is the most time-consuming of all, its removal from the control mode results in significant savings in the time interval necessary to process the patient-generated signals. There are, as one might expect, certain sacrifices that must be made in order to achieve this speed-up in signal processing time, and these manifest themselves in a slightly reduced ability to discriminate among the several limb functions. However, so far these problems have not proven to be serious if adequate normalization is performed.

As will appear presently, an ancillary, but nonetheless significant advantage of the present invention is the ability to reduce response time of the limb to the amputee's brain actuation command by reason of the fact that the entire limb function identification phase of the method can be performed during calibration. Furthermore, as a possible alternative, one may even perform calibration on a separate computer, in a clinic rather than on an amputee-borne device, to reduce weight and cost of the system, assuming of course that suitable facilities are readily available. By using a fixed base calibration computer to perform the identification phase of the method, the analogous hardware need not be carried by the patient, which of course lightens his or her load. On the other hand, provision must be made for restoring in the memory of the patient-borne microprocessor those function identification parameters computed by the fixed base calibration computer. Providing for the latter storage capability is, as would be expected, considerably less costly, lighter and less bulky than the patient-borne calibration equipment it replaces.

It is therefore a still further object of the present invention to provide an improved EMG-actuated system for controlling the movements of an artificial limb, wherein the entire limb function identification phase of the method is performed by a fixed base calibration computer, thus eliminating the need for the patient to include equipment for performing this operation in his or her on-board microprocessor.

The most important advantage of the improved system of the present invention is the much shorter time interval required to initiate a given prosthesis function following receipt of the triggering EMG signals from the patient.

Still another object is the provision of a system of the type aforementioned wherein the necessary storage hardware that must be added to the patient-borne microprocessor to restore the previously calculated limb function identification parameters is much lighter and less expensive than the calibration hardware it replaces.

In another realization of the system, instead of identifying filter parameters, one identifies partial correlation (PC) parameters. Their identification is faster than that of filter parameters (see Box and Jenkins, "Time Series Analysis", Holden Day, 1970). Hence one can allow identification both for calibration and during normal operation. Here the stored PC parameters are compared with those obtained during normal operation, and the limb function related to the set of those closest to that in the memory is actuated.

BRIEF DESCRIPTION OF THE DRAWINGS

Further objects and advantages of the invention will become apparent from the following description of an exemplary embodiment shown in the accompanying drawings, wherein.

DESCRIPTION OF A PREFERRED EMBODIMENT

In view of the fact that the approach employed in the present invention is concerned with utilizing substantially the entire linear information content of the EMG signal, it is essential that data reduction be employed as far as possible to reduce the dimensionality of the problem without loss of information. This is achieved herein by means of first employing signal identification. Noting that the recorded EMG signal represents in a time series that is essentially stochastic, the algorithm used herein consists of identifying the parameters of the time series that is recorded in terms of an autoregressive (AR) model, given by $$y_k = \sum_{i=1}^{n} \gamma_i y_{k-i} + e_k \qquad \text{Equation (1)}$$

$y_k$ denoting the recorded signal, $\gamma_i$ being the AR parameters, n being the order of the AR model, and $e_k$ being white noise. The use of an AR model in this problem is justified for the following reasons:

(a) It can be proved that stationary time series can be represented by an AR model (6) as in Equation (1). Although the EMG signal is not fully stationary, it has been shown in (3) that this signal is sufficiently stationary per each limb function considered to yield AR parameters whose range of variation with time is adequately small to facilitate discrimination between limb functions.

(b) It can be shown (6) that the minimum parameter linear model of a stationary time series is of the form of an autoregressive-moving average (ARMA) model given by:

$$\sum_{i=0}^{m} \phi_i y_{k-1} = \sum_{j=0}^{p} \theta_j e_{k-j}; \phi_0 = \theta_0 = 1 \quad \text{Equation (2)}$$

where $y_{k-i}$, $e_{k-j}$ are as in Equation (1), $\phi_i$, $\theta_j$ denoting the AR and the moving-average (MA) parameters of the model respectively, m and p being the order of the AR and of the MA parts of the model. Now, via polynomial division (6), Equation (2) can be reduced into Equation (1), the latter not being of minimum order. However, the derivation of the minimum order ARMA parameters is rather lengthy and complex (6, Sec. 12.6) as compared with that of the AR parameters for a low AR order n. Since in the present case computational speed is of utmost importance and since it has been shown in (3) that for the EMG signals considered, n=3 or 4 for adequate discrimination and for obtaining $e_k$ that is almost completely white (uncorrelated) it was decided to employ an AR rather than an ARMA model in the present preferred embodiment.

(c) The linear model as in Equation (1) or Equation (2) is fully optimal only if $y_k$ is Gaussian, and is otherwise only linear-optimal, i.e., the best linear model for $y_k$. Hence, in the non-Gaussian case, a non-linear signal model would be required for fully optimality. However, without prior parameter knowledge, which is not available in the present problem, no identification of an optimal model is possible in the general case, and if it were possible it would be too lengthy and too complex from a computational point of view to be of use in a concrete prosthesis application. Furthermore, one can show that (5) the EMG signal can be considered as an outcome of a sequence of impulses with independent Poisson-distributed intervals passed through a linear filter. Now, since the muscles involved are usually (at biceps or triceps) actuated by a large number of motor units (7), say several hundreds, the average interval above is small compared with the dominant time constant of the linear filter involved. Assuming the practical average interspike interval concerned is of the order of t=100 milliseconds, and assuming that N=200 motor units are involved in the muscle contraction, the Poisson rate is $\lambda = N/t = 2000$. Such a Poisson rate implies (8, Ch. 16) that the EMG signal involved closely fits a Gaussian process, as is well known to workers in this field, to further establish the validity of the linear AR model and make it close to an optimal one. From the above, it is not surprising that adequate limb function separation is facilitated via the present approach, as in (3), and as is further pointed out below.

For the above reasons, and noting the speed, weight and volume constraints mentioned above, the choice of an AR model is, at least, well founded.

The algorithm used for identifying the AR model above is a sequential least squares algorithm as described in Sections 5 and 12.6 of (6). This algorithm can be proved to converge to the true parameters of the signal (6), (9).

Furthermore, its near-maximum-likelihood properties (6) make it a near efficient algorithm and therefore of fastest possible convergence rate (see also (10)), namely, it requires the least number of samples for convergence. This aspect is important, noting the above-mentioned constraint of computational speed, and noting that stationarity of the model of Equation (1) can only be assumed over short time periods, even for calibration purposes. Note that the basic least squares algorithm given in (6) requires, however, a large number of computations per sample, top make inter-sample computation time lengthy. The present invention employs this algorithm only at a calibration mode, whereas no identification per se is performed during normal operation. Note also that use of other identification algorithms, such as sequential learning or stochastic approximations (6), where the number of computations per iteration (per sampling interval) is small, was attempted. However, these algorithms were far too slow to converge in terms of the number of iterations required, such that no discrimination could have been expected within the 0.2 second required for smooth prosthesis actuation, and were therefore abandoned.

The above-recommended procedure of the present invention is employed in the prosthesis control system such that it is run several times (say L times) per each limb function for calibration purposes. The parameters obtained during these identification runs are averaged over the above runs and are stored as sets $(\bar{\gamma}_{11} \ldots \bar{\gamma}_{1n})$; $(\bar{\gamma}_{21} \ldots \bar{\gamma}_{2n}); \ldots (\bar{\gamma}_{h1} \ldots \bar{\gamma}_{hn})$, when h different limb functions are considered, each having n parameters. Once these parameters are stored, another calibration run is made, where the EMG signals $y_{k,i}$ (k=1 ... N, denoting time interval) related to function i (i=1 ... h) are fed to an algorithm (i.e., a filter) that computes:

$$\hat{y}_{kj} = \bar{\gamma}_{j1} y_{k-1} + \bar{\gamma}_{j2} y_{k-2} + \ldots \bar{\gamma}_{jn} y_{k-n}; j=1, \ldots h \quad \text{Equation (3)}$$

Alternatively, one may compute $\hat{y}_k$ from the ARMA model of Equation (2) above, to yield:

$$y_k - \hat{y}_{ki} \stackrel{\Delta}{=} \hat{e}_{kj} \quad \text{Equation (4)}$$

($y_k$=the actual EMG signal at the k-th time interval)
Defining:

$$E_j \stackrel{\Delta}{=} \frac{\sum_{k=n+1}^{N+n} \hat{e}_{kj}^2}{\sum_{k=n+1}^{N+n} y_k^2}; j = 1, \ldots, h \quad \text{Equation (5)}$$

and averaging over L runs, now yields $\bar{E}_1 \ldots \bar{E}_h$ for limb functions 1 to h, which are stored in the memory of the microcomputer.

Normal Operation Mode

Figure 1:
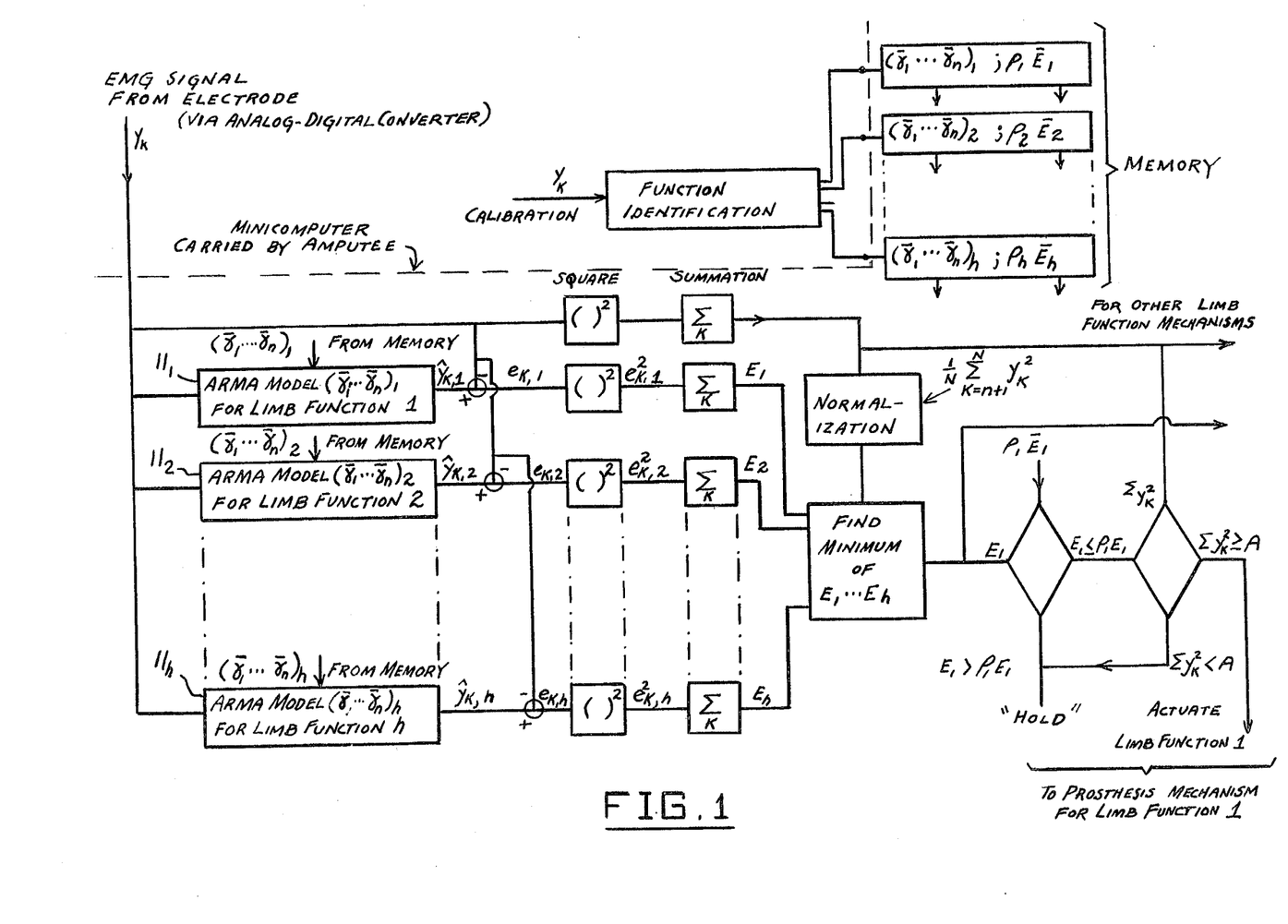
FIG. 1 is a generalized block diagram of apparatus according to the present invention for controlling an artificial limb via identification and discrimination of EMG signals.

The calibration procedure above described is performed clinically, namely, prior to normal usage of the prosthetic appliance. Subsequently to the above-described calibration, the microcomputer of the appliance is ready to perform the limb function discrimination and activate an intended limb function i during normal limb-operation (usage), as follows: The measured EMG signal $y_k$ (in digital form) is fed in parallel to filters (ARMA models 1 ... h), shown schematically at $11_1$ to $11_h$, to compute $\hat{e}_{k1}$ to $\hat{e}_{kh}$, as in Equation (3) and Equation (4). By squaring and summing, $E_1 ... E_h$ are then computed. The minimum of $E_1 ... E_h$ is then found by the minicomputer, and, after normalization with respect to $$\frac{1}{N} \sum_{k=n-1}^{N} y_k^2,$$

the resultant minimum $E_j \overset{\Delta}{=} E_i$ is compared with the previously stored $\overline{E}_i$ of the memory, i.e., as averaged over the L calibration runs yielding $\overline{E}_1 ... \overline{E}_h$ for limb functions 1 to h, as above described. Finally, as a result if $$E_i \leq \rho_i \overline{E}_i,\qquad \text{Equation (6)}$$

where $\rho_i$ is a weight coefficient greater than 1 ($\rho_i \overline{E}_i$ having been previously derived and stored in the memory during the calibration mode), and if $$\sum_{k=1}^{M} y_k^2 \geq A \qquad \text{Equation (7)}$$

where M is the number of $y_k^2$ terms, and where A is a predetermined constant (to prevent actuation for a low $E_1$ due to a situation where no EMG signal is measured), then limb function i (the intended limb function) of the limb functions 1 ... h is actuated. Otherwise, the prosthesis will be or remain in a "hold" mode.

The operational system above described is shown in block diagrammatic form in FIG. 1. For increasing the operating speed, suitable fast hardware multipliers may be used in the hardware realization of FIG. 1, especially in the amputee-carried portion of the system.

Note that the system of the present invention involves only simple filtering, namely multiplication and addition, rather than identification during normal prosthesis use (during normal operation), whereas identification is solely performed during calibration. Hence, since identification is the most time consuming part of the system, this provides a considerable time saving during normal operation. Discrimination may be somewhat sensitive via this approach, in certain situations, i.e., when the parameters employed are somewhat biased due to incomplete convergence, or to wrong model order. Hence, if an identification-bias exists, the method of comparing parameters in a parameter vector space, as in (3), or in U.S. Pat. No. 4,030,141, may be advantageous. (Note, however, that in the discrimination approach of (3), discrimination must be exact if $\overline{\gamma}=\hat{\gamma}$, whereas in the system of the present invention this is not necessarily so, since the minimal error-variance may occur for the wrong limb-function due to the identification bias.). However, since in the system of the present invention identification is performed only during calibration and not during normal operations, sufficient computation time is usually available to reach convergence such that biases can be eliminated.

Furthermore, assuming access to calibration computers is adequate, the whole calibration top portion of FIG. 1 can be, though need not be, performed in a clinic, such that the related hardware will not be worn by the patient, so as to greatly reduce weight and cost. This, however, requires adequate facilities for re-storing the parameters of the amputee-carried portion of the system of FIG. 1, namely $(\gamma_1 ... \gamma_n)_i$ and $\rho_i \overline{E}_i$ for $i = 1 ... h$ in the memory of the patient-borne microprocessor system as computed by the calibration computer in the clinic.

Figure 2:
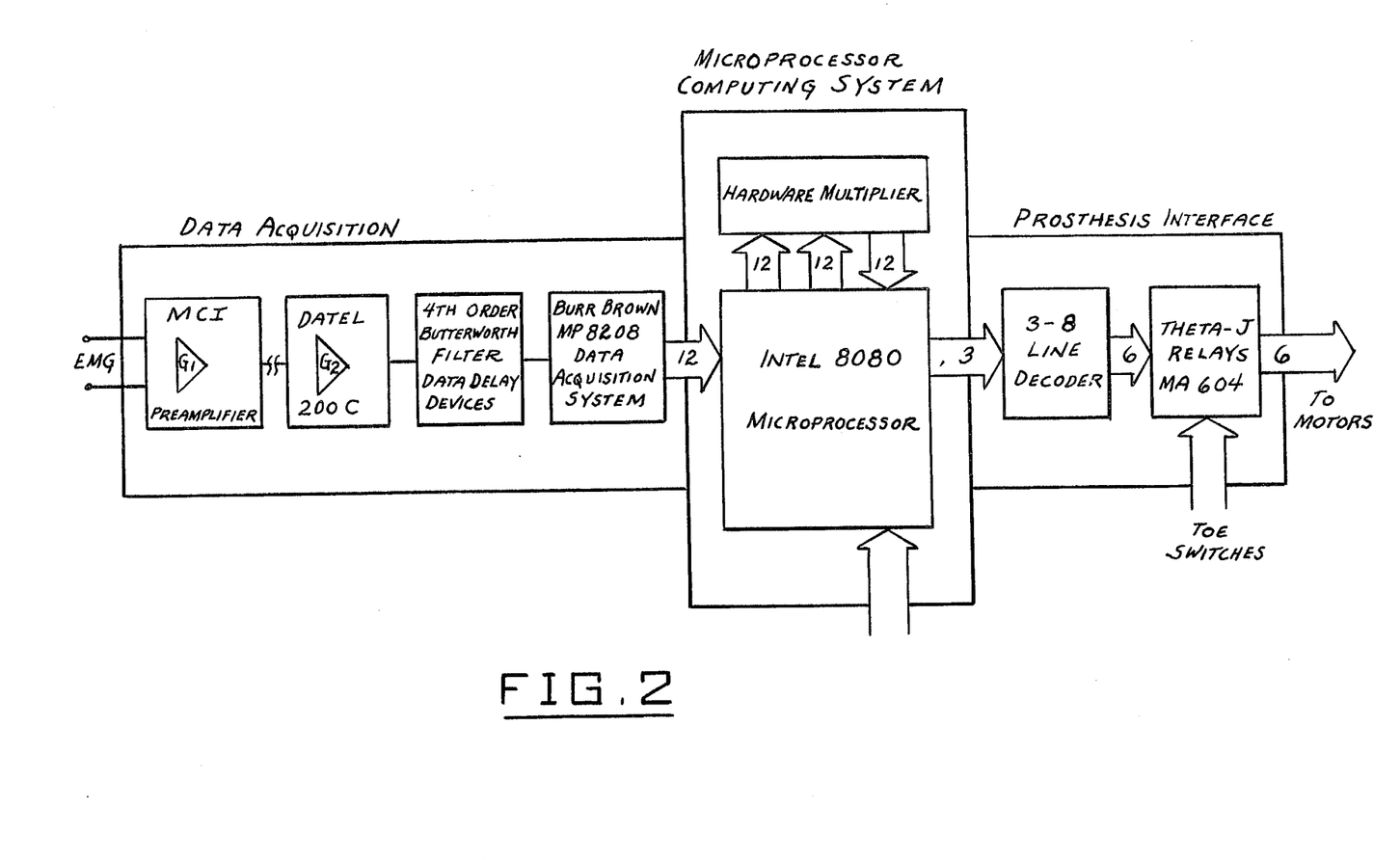
FIG. 2 is a block diagram of a practical prosthesis system employing a control system according to FIG. 1.

In a typical practical embodiment of the present invention shown in FIG. 2, the system of FIG. 1 is employed for only five functions (j = 1, 2, 3, 4, 5 above), whereas grasp movement is produced by toe-actuation, as in (4). Furthermore, the movement is used to interrupt operation if discrimination turns out to be wrong, or to facilitate speed control. The above-described system thus facilitates speed and torque control. A design for all seven functions has been formulated, which may employ two parallel microprocessor systems, or a single very fast microprocessor, where computations of the tasks of the two parallel systems above can be done in series. The typical five-function system employs only a single set of electrodes, whereas the seven-function systems presently employs two sets of electrodes, which thus requires two parallel systems.

The above-mentioned five-limb function system, involving one set of electrodes for discriminating and controlling five limb functions, feeds to a motor control and actuation unit similar to that of the toe-controlled system of (4), and a schematic block diagram thereof is shown in FIG. 2.

In the system of FIG. 2, data acquisition is performed as follows: The EMG signal is obtained via an EMG preamplifier unit manufactured by Motion Control Inc., (MCI). Disc type electrodes are mounted directed on the preamplifier module, which is therefore located directly above the muscle being monitored. Due to the preamplification directly above the monitored muscle, the above unit facilitates a higher signal-to-noise ratio after transmission, than is usually achieved by other surface electrodes. The preamplifier weighs only 8 grams and does not require the use of conductive jelly that is often used and is usually very inconvenient and unreliable.

The preamplified EMG signal is fed to a Datel 200C instrumentation amplifier for further amplification. Undesirable frequencies are filtered out by a 4th order Butterworth bandpass filter (with a passband between 1.5 and 1,500 Hz) produced by Data Delay Services. A 12-bit data acquisition system, the Model MP8208, produced by the Burr Brown Research Corporation, samples the EMG signal at a rate of 5000 samples per second, and delivers the digital data to the microprocessor computer system.

The microprocessor system of FIG. 2 is based on an 8080 Intel Corporation microprocessor, which is an 8-bit parallel central processing unit (13). It is fabricated on a single LSI chip using recent advances in N-channel silicon gates and is furnished in a 40-pin dual in-line ceramic package, having a 2-microsecond instruction time (for instructions that do not refer to memory). The above 8080 microprocessor is then interfaced with its input-output ports and with a 4K-bytes semiconductor memory. Furthermore, to increase speed and, since the multiply and divide instructions are the most time consuming ones in the program, the microprocessor is also interfaced with a hardware multiplier unit based on a Fairchild 9344 4×2 bit multiplier modules where multiplication time is 350 n-seconds vs. 1 m-second in the microprocessor itself. Note that since no division is made during normal operation, hardware division is not presently performed. Via the latter arrangement, the complete recognition is performed within 0.2 seconds for the five function system, namely, within the desired speed limit.

It is to be noted that even with hardware presently available, such as the Intel 3000 system, a ten-times faster system can be achieved than was previously possible, using the same algorithms as above. Observing that 12-bit data are used, the 8-bit 8080 program is in terms of double word length.

The interface between the microprocessor computing system and the prosthesis is basically similar to that of the toe-controlled prosthesis of (4). It is to be noted that the system of the present invention may also incorporate toe control as in (4) for interrupt, speed control, and grasp. The latter functions may alternatively be performed via processing EMG data from two electrode locations, using either two microprocessors in parallel or one fast microprocessor operating in a multiplex mode.

Figure 3:
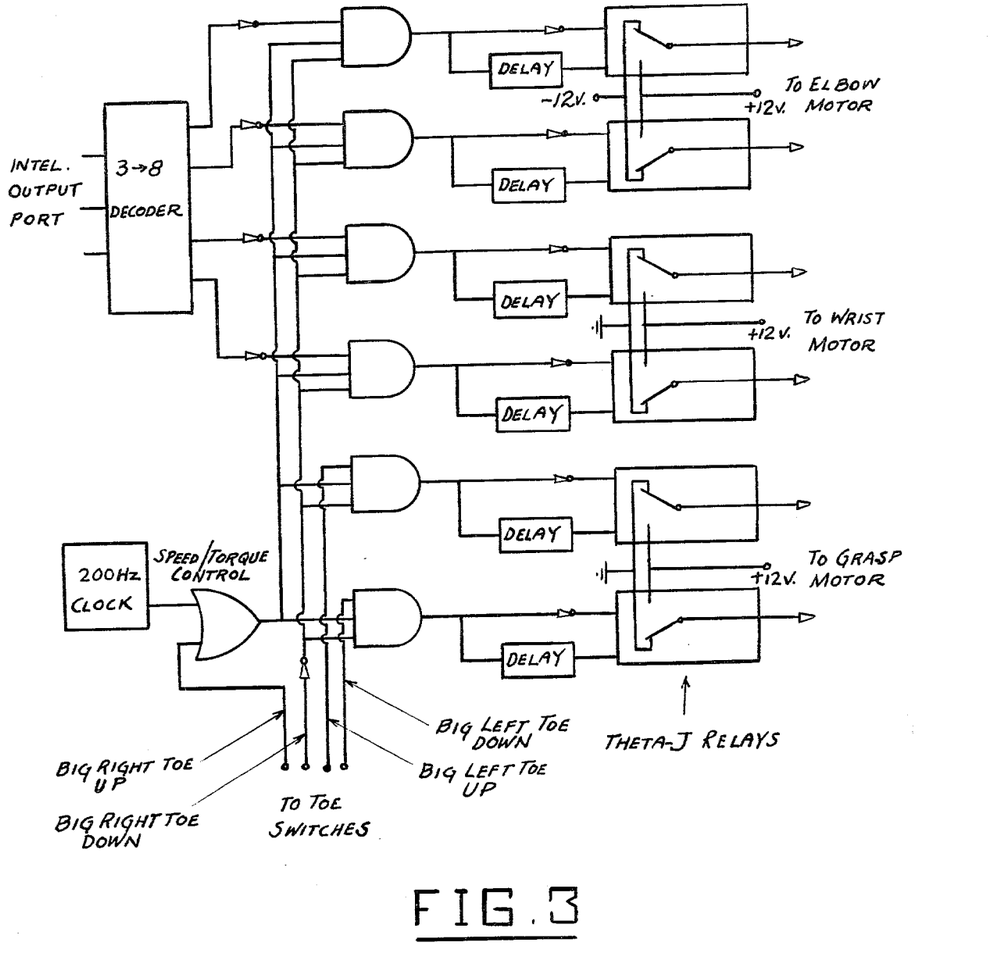
FIG. 3 is a schematic wiring diagram of the prosthesis interface portion of the system of FIG. 2.

The microprocessor computing system latches the binary function code into an output port, from where it is decoded by a 3-to-8 line decoder. The TTL-signals from the decoder control directly power DIP solid state DC relays (MA-604 manufactured by Theta-J Relays, Inc.) which switch the power to the prosthesis motors, as shown in FIG. 3.

From the foregoing description it will be seen that both the present invention and that forming the subject matter of U.S. Pat. No. 4,030,141 are based substantially upon the same theoretical approach, namely, the identification of an autoregressive (AR) model or an autoregressive moving average (ARMA) model of the electromyographic signal, and upon using the information thus acquired as the basis of discriminating among the several possible limb functions and actuating the prosthesis in accordance therewith. The system of the present invention, as that of U.S. Pat. No. 4,030,141, demands identification of either a minimum parameter ARMA model or a pure AR model of the EMG signal related to the various limb functions to be controlled. These parameters are obtained from the patient during the first part of the clinical calibration phase of the method, and they constitute an average of several runs. Once obtained, these parameters are stored in the patient-borne memory as sets $(\bar{\gamma}_{11} \ldots \bar{\gamma}_{1n})$; $(\bar{\gamma}_{21} \ldots \bar{\gamma}_{2n})$; $\ldots (\bar{\gamma}_{h1} \ldots \bar{\gamma}_{hn})$.

Having obtained and stored these parameters in the microprocessor memory of the patient, another calibration run is made, constituting a second part of the clinical calibration phase of the method, where the EMG signals $y_{k,i}$ ($k=1\ldots N$, denoting time intervals) related to function i ($i=1\ldots h$) are each fed to an algorithm, as above described, and are processed to derive the $\rho_i \bar{E}_i$ data, which is likewise stored in the patient-borne memory.

Here, of course, is where the system of the present invention differs from U.S. Pat. No. 4,030,141, in that instead of making near simultaneous identification of the limb function to be actuated just prior to initiating same with a patient-borne microprocessor, the calibration necessary to discriminate among a given patient's several limb functions is accomplished ahead of time with a fixed base calibration computer, and only the predetermined results of such limb function identification are transferred to the patient by storing them in the memory of the patient-borne microprocessor. Thus, the patient still carries the information necessary to perform limb function discrimination as before, but in a predetermined form where the instantaneously developed, or current, EMG signal need only be compared with the stored data in order to initiate or hold the prosthesis function thus singled out.

More specifically, as above described, in operation the instantaneously developed current EMG signal $y_k$ is fed to the patient-borne microprocessor via an analog-digital converter where it is fed in parallel to algorithms (ARMA models) $11_1$ to $11_h$ for each of the limb functions $1 \ldots h$ so as to compute $\hat{e}_{k1}$ to $\hat{e}_{kh}$. The patient-borne microprocessor processes the digitized incoming signal $y_k$ received from the electrode carried by the patient's limb stump through each of the several limb functions to be controlled and compares the resulting sets with the corresponding sets stored in its memory. As $\hat{y}_k$ for each of the limb functions $1 \ldots h$ is thus determined and compared with the current incoming EMG signal $y_k$, as shown in FIG. 1, then the value for $e_k$ emerges for each such function. $E_i$ values are then computed, as shown in FIG. 1, and the minimum of $E_1 \ldots E_h$ is found and normalized with $$\frac{1}{N} \sum_{k=n+1}^{N} y_k^2$$

as above described. Finally, if $E_i \leq \rho_i \bar{E}_i$, where $\rho_i$ is a constant $>1$, then the limb function i of the limb function set $1 \ldots h$ is actuated, provided that $$\sum_{k=1}^{M} y_k^2 \geq A.$$

Conversely, if $E_i > \rho_i \bar{E}_i$ or $$\sum_{k=1}^{M} y_k^2 < A,$$

then the limb function i of the limb function set $1 \ldots h$ will return to, or remain in a "hold" mode.

It should be noted that processing of the $e_k$ signals for each limb function $1 \ldots h$ involves only simple filtering operations, i.e., multiplication and addition, to arrive at values for $E_1 \ldots E_h$, that are readily processed to determine the minimum thereof $(E_i)$, which is then compared with the corresponding $\rho_i \bar{E}_i$ from the patient-borne memory. The resulting comparison either actuates limb function i of the limb function set $1 \ldots h$ in the prosthesis or holds, as the case may be.

Thus, the system of the present invention has the same optimal or linear optimal features and minimum parameter features as that disclosed in U.S. Pat. No. 4,030,141. However, it overcomes the overwhelming difficulties associated with the prior art attempts as multi-functional EMG control via the same theory and realization approach; it uses an alternative limb function discrimination method again based on the same theory, but having substantial speed, weight and cost advantages. Essentially it involves simple filtering, namely, multiplication and addition, rather than identification in the control mode, whereas identification is solely done during calibration. Hence, since identification is the most time-consuming part of the system, this implies a considerable time saving.

In the alternative realization, the PC parameters $\phi_{ii}$ identified during calibration and during normal operation, are given by (see G.E.P. box and G. M. Jenkins, "Time Series Analysis", Holden Day, San Francisco, 1970, Ch. 3):

$$\delta_j = \phi_{k1}\delta_{j-1} + \cdots \phi_{k(k-1)}\delta_{j-k}; j=1, 2, \ldots k$$

where $\delta_j \triangleq (\gamma_j/\gamma_0)$; $\gamma_i \triangleq E[y_k y_{k-j}]$, E denoting expectation.

While a specification embodiment of an improved system for multifunctional control of upper limb prosthesis via EMG signal identification has been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiment.

What is claimed is:

1. In a method for controlling the operation of an electrically powered prosthesis appliance that replaces an amputee's missing limb which method includes calibration steps of picking up electromyographic (EMG) signals from the stump of or from at least one muscle close to the point of amputation of the missing limb, and processing the signals thus collected as to reduce same to a near minimum number of linear time-series model parameters effective to differentiate between each of the several functions performed by the missing limb from each other function thereof, and collecting historical data representative of each of the functions of the prosthesis appliance to be controlled for use as background data, the improvement comprising storing the parameters and the background data of each of the functions to be performed by the prosthetic appliance on the person of the amputee, collecting current EMG signals from the stump of the amputee or from at least one muscle close to the point of amputation and passing same simultaneously through several electronic networks having a common input and each having been adjusted by the stored time-series parameters relating to a different limb function as obtained during calibration, and comparing the current EMG signals collected with the outputs of each of said networks, and initiating a response in the prosthetic appliance corresponding to that network whose output over a predetermined time interval is closest to the collected EMG signals over the same time interval.

2. The improved method as set forth in claim 1, wherein the stored background data constitutes processed EMG signals averaged over several runs during which the amputee performs the several functions to be performed by the prosthetic appliance.

3. The improved method as set forth in claim 1, wherein the current EMG signals are repeatedly sampled, processed and compared with the stored historical data during an interval over which said signals remain substantially stationary.

4. The improved method as set forth in claim 1, wherein the stored background data constitutes processed EMG signals averaged over several runs during which the amputee performs the several functions to be performed by the prosthetic appliance, and wherein the historical data thus averaged is stored as sets of parameters $(\bar{\gamma}_{11} \ldots \bar{\gamma}_{1n}); (\bar{\gamma}_{21} \ldots \bar{\gamma}_{2n}) \ldots (\bar{\gamma}_{h1} \ldots \bar{\gamma}_{hn})$, where h is the number of limb functions and n is the number of parameters necessary to discriminate among the several limb functions.

5. The improved method as set forth in claim 4, wherein historical EMG data (y) developed by the amputee and related to time ($y_k$), where $k=1 \ldots N$, is processed using the stored sets for each limb function in accordance with the following algorithm to yield ($y_{k,j}$), where $j=1 \ldots h$ $$\hat{y}_{k,j} = \bar{\gamma}_{j1} y_{k-1} + \bar{\gamma}_{j2} y_{k-2} + \ldots \bar{\gamma}_{jn} y_{k-n},$$

wherein a term $e_k$ for a given limb function is determined by subtracting $\hat{y}_k$ for that limb function from $y_k$ therefore, where $y_k$ represents the actual EMG signal at the k-th time interval, and wherein $e_k$ for each limb function is further processed in accordance with the following formulas:

$$e_k = y_k - \hat{y}_k$$

to yield a term $E_j$ which is a normalized function of $e_k$ above for limb function $j=1, 2, \ldots h$, for each limb function.

6. The improved method as set forth in claim 5, wherein ($^{min}E_i$), the minimal E from $E_1$ to $E_n$, is compared with stored background data $\rho_i \bar{E}_i$, where $\rho_i$ is a weight coefficient greater than 1, and wherein if ($^{min}E_1$) is $\leq \rho_i \bar{E}_i$ the limb function i of the set $1 \ldots h$ is initiated.

7. The improved method as set forth in claim 6, and wherein the limb function is not initiated unless $$\sum_{k=1}^{M} y_k^2 \geq A,$$

where A is a predetermined constant and M is the number of $y_k^2$ terms.

8. The improved method set forth in claim 7, and wherein if $E_i$ is low due to non-measurement of an EMG signal the prosthesis appliance is placed in a "hold" mode.

9. The improved method of claim 8, and wherein the storing of the background data comprises a first series of calibration runs for deriving and storing the sets of parameters $(\bar{\gamma}_{11} \ldots \bar{\gamma}_{1n}); (\bar{\gamma}_{21} \ldots \bar{\gamma}_{2n}) \ldots (\bar{\gamma}_{h1} \ldots \bar{\gamma}_{hn})$ for h different limb functions and a second series of calibration runs for deriving and storing $\rho_i \bar{E}_i$.

10. The improved method of claim 9, and wherein the stored $\bar{E}_i$ terms are averaged over the second series of calibration runs from the expression $$E_j \triangleq \frac{\sum_{k=n+1}^{N+n} e_{kj}^2}{\sum_{k=n+1}^{N+n} y_k^2}$$

where $j=1 \ldots h$.

11. A method as in claim 1, wherei in the parameters are partial correlation (PC) parameters, and where comparison of current data with stored data relates to measuring distances in some sense between the current set of PC parameters and any set in memory, such that the smallest distance determine the limb function to be actuated.

12. The method as in claim 1, and wherein the steps up to and including storing and data, is performed on a computer in a clinic or laboratory and no on the amputee-borne system.

13. In a system for controlling the operation of an electrically powered prosthetic appliance that replaces an amputee's missing limb, which system has been pre-calibrated by calibration steps of picking up electomyographic (EMG) signals from the stump of or from at least one muscle close to point of amputation of the missing limb, processing the signals thus collected so as to reduce same to a near minimum number of linear time series model parameters effective to differentiate between each of the several functions performed by the missing limb from each other function thereof, and collecting historical data representative of each of the functions of the prosthesis appliance to be controlled for use as background data, the improvement comprising means for storing the parameters and the background data of each of the functions to be performed by the prosthetic appliance on the person of the amputee; means for collecting current EMG signals from the stump of the amputee or from at least one muscle close to the point of amputation; a plurality of networks having a common input coupled to receive the collected current EMG signals, each said network having been adjusted by the stored time series parameters relating to respective different limb functions as obtained during calibration; comparing means for comparing the current EMG signals collected with respective outputs of said networks; and means responsive to output from said comparing means for initiating a response in the prosthetic appliance corresponding to that network whose output over a predetermined time interval is closest to the collected EMG signals over the same interval.

* * * * *